US012773304B2

(12) United States Patent
Wiart

(10) Patent No.: US 12,773,304 B2
(45) Date of Patent: Oct. 27, 2026

(54) SELF-REMOVING ANIMAL DART

(71) Applicant: 1346369 Alberta Ltd., Ponoka (CA)

(72) Inventor: Gene Wiart, Ponoka (CA)

( * ) Notice: Subject to any disclaimer, the term of this patent is extended or adjusted under 35 U.S.C. 154(b) by 1107 days.

(21) Appl. No.: 17/749,090

(22) Filed: May 19, 2022

(65) Prior Publication Data

US 2023/0032234 A1 Feb. 2, 2023

Related U.S. Application Data

(60) Provisional application No. 63/190,242, filed on May 19, 2021.

(51) Int. Cl.

*A61D 7/00* (2006.01)
*A61M 5/20* (2006.01)

(52) U.S. Cl.

CPC ................. *A61D 7/00* (2013.01); *A61M 5/20* (2013.01)

(58) Field of Classification Search

CPC ............ A61M 2250/00; A61M 5/3269; A61M 2005/2013; A61M 5/3243; A61M 2005/3252; A61M 2005/3228; A61M 5/321; A61M 2005/14506; A61M 2005/14513; A61M 5/1452; A61M 5/14526; A61M 2005/14533; A61M 5/1454; A61M 2005/1583; A61M 5/3213; A61M 5/3219; A61M 5/322; A61M 5/3232; A61M 5/3234; A61M 2005/3235; A61M 2005/3236; A61M 2005/3238; A61M 2005/3239; A61M 5/3245; A61D 7/00; F42B 12/54; F42B 12/36; F42B 12/362; F42B 6/003; F42B 5/105; F41B 11/85

See application file for complete search history.

(56) References Cited

U.S. PATENT DOCUMENTS

| | | | | |
|---|---|---|---|---|
| 2005/0159706 A1* | 7/2005 | Wilkinson | ............ | A61M 5/326 604/110 |
| 2009/0259201 A1* | 10/2009 | Hwang | ............ | A61B 5/150648 604/263 |
| 2011/0152832 A1* | 6/2011 | Foshee | ................ | A61M 5/3275 604/506 |
| 2019/0249965 A1* | 8/2019 | Wiart | ....................... | A61D 7/00 |

FOREIGN PATENT DOCUMENTS

| | | | |
|---|---|---|---|
| KR | 20190127009 A * | 11/2019 | ............. A61M 5/30 |

* cited by examiner

*Primary Examiner* — Lauren P Farrar
*Assistant Examiner* — Guillermo G Paz Estevez
(74) *Attorney, Agent, or Firm* — Sander R. Gelsing

(57) ABSTRACT

In one aspect there is provided a self-removing animal injection apparatus for injecting an animal with a liquid medication. The apparatus comprises a shaft having a first end and a syringe. A needle is provided at the first end of the shaft and defines a longitudinal direction. The needle is in fluid communication with the syringe. First and second disengaging members are movable substantially along the longitudinal direction and operable to assist with disengagement of the animal injection apparatus from the animal, once at least some of the liquid medication has been injected into the animal.

2 Claims, 10 Drawing Sheets

SELF-REMOVING ANIMAL DART

CROSS REFERENCE TO RELATED APPLICATION

This application is a non-provisional application which claims priority to, and benefit of, U.S. Provisional Patent Application Ser. No. 63/190,242 filed May 19, 2021 and entitled, "SELF-REMOVING ANIMAL DART", the entirety of which is incorporated herein by reference.

FIELD OF THE INVENTION

This invention relates generally to an animal syringe system for injecting animals at a distance away from the animal. More particularly, the invention relates to a self-removing animal dart for the automatic withdrawal or disengagement of the syringe from the animal once medication delivery is complete.

BACKGROUND OF THE INVENTION

The background information discussed below is presented to better illustrate the novelty and usefulness of the present invention. This background information is not admitted prior art.

In U.S. Patent Application No. 2019/0249965 a range animal injection apparatus is described. This apparatus has a syringe, a pressure chamber, a needle and a self-removal system which may include a contact member positioned only on one side of the needle and projections extending from an end of the dart. When the apparatus hits an animal the contact member is pushed back opening a valve at the needle end of the syringe. Pressure in the pressure chamber acts on the plunger of the syringe pushing medication into the animal. The plunger eventually closes the valve and moves the contact member forward to remove the apparatus from the animal. Pinching is reduced by the contact member being positioned below and not around the needle. The projections help keep the dart relatively perpendicular to the hide reducing pinching and increasing leverage. The projections also reduce rotation of the apparatus, helping to keep the contact member below the needle.

While this apparatus has been generally successful, more reliability is desired. For example, sometimes the pressure exerted by the contact member against the animal's hide is insufficient to fully disengage the dart from the animal, thereby preventing the dart from promptly dropping away from the animal once the medication has been delivered.

SUMMARY OF THE INVENTION

In an embodiment of the invention, there is provided a self-removing animal injection apparatus for injecting an animal with a liquid medication. The apparatus comprises a shaft having a first end and a syringe. A needle is provided at the first end of the shaft and defines a longitudinal direction. The needle is in fluid communication with the syringe.

A first disengaging member is movable substantially along the longitudinal direction and operable to assist with disengagement of the animal injection apparatus from the animal, once at least some of the liquid medication has been injected into the animal.

A second disengaging member is movable substantially along the longitudinal direction and operable to assist with disengagement of the animal injection apparatus from the animal once at least some of the liquid medication M has been injected into the animal.

BRIEF DESCRIPTION OF THE DRAWINGS

Referring to the drawings, several aspects of the present invention are illustrated by way of example, and not by way of limitation, in detail in the figures, wherein.

DETAILED DESCRIPTION OF THE PREFERRED EMBODIMENTS

Figure 1:
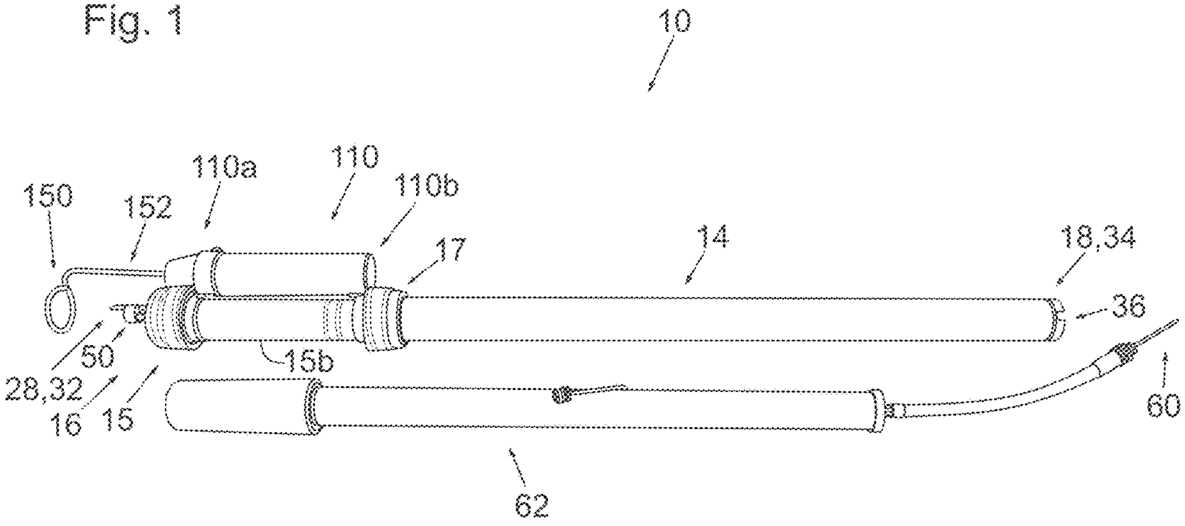
FIG. 1 is a perspective view of a first embodiment of a self-removing animal dart, along with a conventional air pump.

The following description is of preferred embodiments by way of example only and without limitation to the combination of features necessary for carrying the invention into effect. Reference is to be had to the Figures in which identical reference numbers identify similar components. The drawing figures are not necessarily to scale and certain features are shown in schematic or diagrammatic form in the interest of clarity and conciseness.

Figure 2:
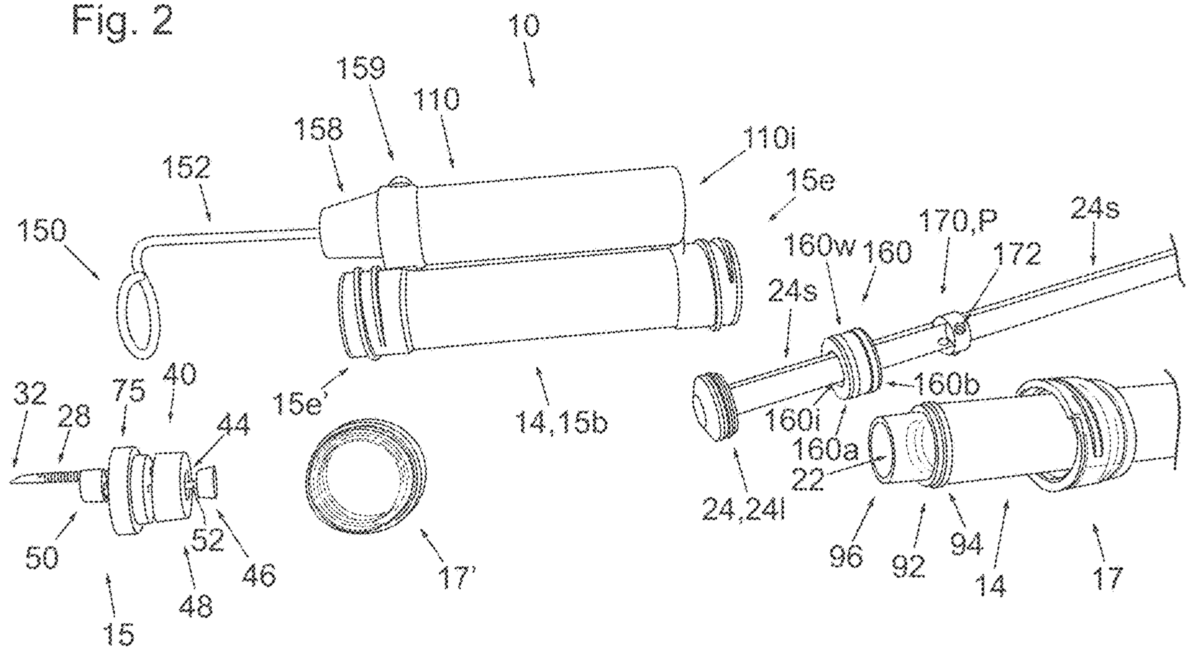
FIG. 2 is an exploded perspective view of the self-removing animal dart of FIG. 1.

A first embodiment of a self-removing range animal injection apparatus or self-removing animal dart 10 is shown in FIGS. 1-2. A second embodiment of the self-removing animal dart 10 is shown in FIGS. 3-7. In this document the term "dart" will be used to encompass "arrow", "dart" and any other form of suitable projectile to deliver an animal syringe system and carries no implication as to delivery method. In a preferred embodiment, the dart 10 is configured to be shot from a crossbow (not shown) towards an animal that is to be injected with liquid medication M (which may be clear or transparent). In this document the terms "leading" and "trailing" will be used respectively to refer to those parts on the dart 10 that are closest to the animal ("leading") versus those parts on the dart 10 that are furthers ("trailing") from the animal when the dart 10 is aimed or shot at an animal. The dart 10 could also be made larger and mounted on a pole or made smaller and shot from a dart gun.

Referring to the figures, the dart 10 of these embodiments has a shaft 14 with a syringe 15 positioned at a first (leading) end 16 of the shaft. Preferably the syringe 15 comprises a syringe barrel 15*b* having an interior 15*i*. More preferably, syringe barrel 15*b* is attached to, or forms, the leading portion of the dart's shaft 14 and said first end 16. A needle 28 is secured to the first end 16 of the shaft 14 (and hence the syringe 15). Needle 28 has a first end 30 and a second end 32. First end 30 of the needle communicates with a syringe chamber 20 within the syringe barrel 15*b* through a valve 40 (see FIG. 7). Second end 32 projects past first end 16 of shaft 14 and may be the needle's tip. Syringe barrel 15*b* may have a first (trailing) threaded end 15*e* and be threadably, sealably connected to a first pressure chamber 22 in the shaft 14 via a first threaded connector 17. First pressure chamber 22 is preferably constructed in a conventional manner and of suitable material (e.g. moulded plastic or steel) to provide adequate strength, durability, sealability and rigidity to support the various loads and pressures that may be encountered and/or required to actuate the various components of the dart 10.

Shaft 14 has a hollow internal cavity forming the first pressure chamber 22. A plug 34 is disposed at second (trailing) end 18 of shaft 14 with a self-sealing passage 36 therethrough. Passage 36 is adapted to receive a needle valve 60 so that air, or other source of pressure, can be pumped or injected under pressure into the first pressure chamber 22. This pressurized air may then be held or contained within the first pressure chamber 22 and may act upon a reciprocating first piston or plunger 24 of the syringe 15, and may providing a motive force to actuate the various components of the dart 10 as further described below.

The syringe's plunger 24 preferably further comprises a plunger head, stopper or seal 241 and a plunger shaft 24*s*. Plunger seal 241 is at a leading end 24*a* of the plunger shaft 24*s* and is sealably disposed between the first pressure chamber 22 and the syringe chamber 20 (see FIGS. 4 and 7). The remaining (trailing) portion of the plunger shaft 24*s*, including its trailing end 24*b*, is disposed into the first pressure chamber 22. The plunger seal 241 fits tightly within the syringe barrel 15*b* and functionally separates the syringe chamber 20 from the first pressure chamber 22.

The plunger seal 241 reciprocates within the syringe barrel 15*b*, as is conventional with syringes, thereby also reciprocating the boundaries of the syringe chamber 20 and first pressure chamber 22. Similarly, the plunger shaft 24*s* reciprocates within the syringe barrel 15*b* and the first pressure chamber 22. When a pressure imbalance is created between syringe chamber 20 and first pressure chamber 22, plunger 24 will reciprocate accordingly. For example, if there is a greater pressure in the first pressure chamber 22 (e.g. due to air injected into said chamber 22), this will act on the plunger seal 241 and move said seal 241 to compress and shorten syringe chamber 20. As further described below, this may then force any liquid medication M from syringe chamber 20 through needle 28.

The self-removing animal dart 10 further comprises a valve 40 positioned adjacent first end 30 of needle 28. The valve 40 may be actuatable between an open position and a closed position and be as described in U.S. Patent Application Publication No. 2019/0249965 and include a valve seat member 48 defining, passage 44 and a pressure sensitive valve member 46 movable axially in relation to passage 44 between an open position and a closed position. When valve 40 is in the open position, illustrated in FIGS. 2, 5, 6*b*, 6*c* and 6*f*-6*i*, valve member 46 is spaced from passage 44 thereby allowing the free flow of liquids from syringe chamber 20 through the valve 40 to needle 28. When valve 40 is in the closed position, illustrated in FIGS. 1,4, 6*a*, 6*d*-6*e*, 6*k*-6*l* and 7, valve member 46 is lodged in passage 44 thereby creating a fluid-tight seal and precluding the flow of liquids from syringe chamber 20 to needle 28. To create a fluid-tight seal the valve seat member 48 and/or the valve member 46 may be formed of flexible material and the valve member 48 may be tapered with a maximum circumference slightly larger than the maximum circumference of the passage 44.

A first contact member 50 is movable axially in relation to needle 28 along a longitudinal direction between first end 30 and second end 32 of the needle. One function of the first contact member 50 is to actuate the valve, as further described below. The first contact member 50 also functions to disengage, or assist with the disengagement of, the dart 10 from an animal (not shown). Pressurized air in the first pressure chamber 22 may provide the motive force (directly or indirectly) to power and allow the first contact member 50 to disengage the dart 10 from an animal (as further described below).

A first rigid coupling 52, which may be a rod, couples the movement of first contact member 50 and valve member 46. Rigid coupling 52 may be threadably connected to valve member 46. In an embodiment, first contact member 50 is preferably positioned so the first contact member 50 is below the needle 28 when the needle 28 is inserted into the animal (e.g. as in FIG. 1). In another embodiment, first contact member 50 is preferably positioned so the first contact member 50 is above the needle 28 when the needle 28 is inserted into the animal (e.g. as in FIG. 7). Preferably, the first contact member 50 is positioned at or near a center axis A of the shaft (14) of the dart 10 and the needle 28 is positioned to one side relative to the center axis A of the dart (see FIG. 4). Center axis A may also be referred to as shaft center axis A or first axis A. The first contact member 50 may then positioned above, below or beside the needle 28 by the user as desired.

Figure 5:
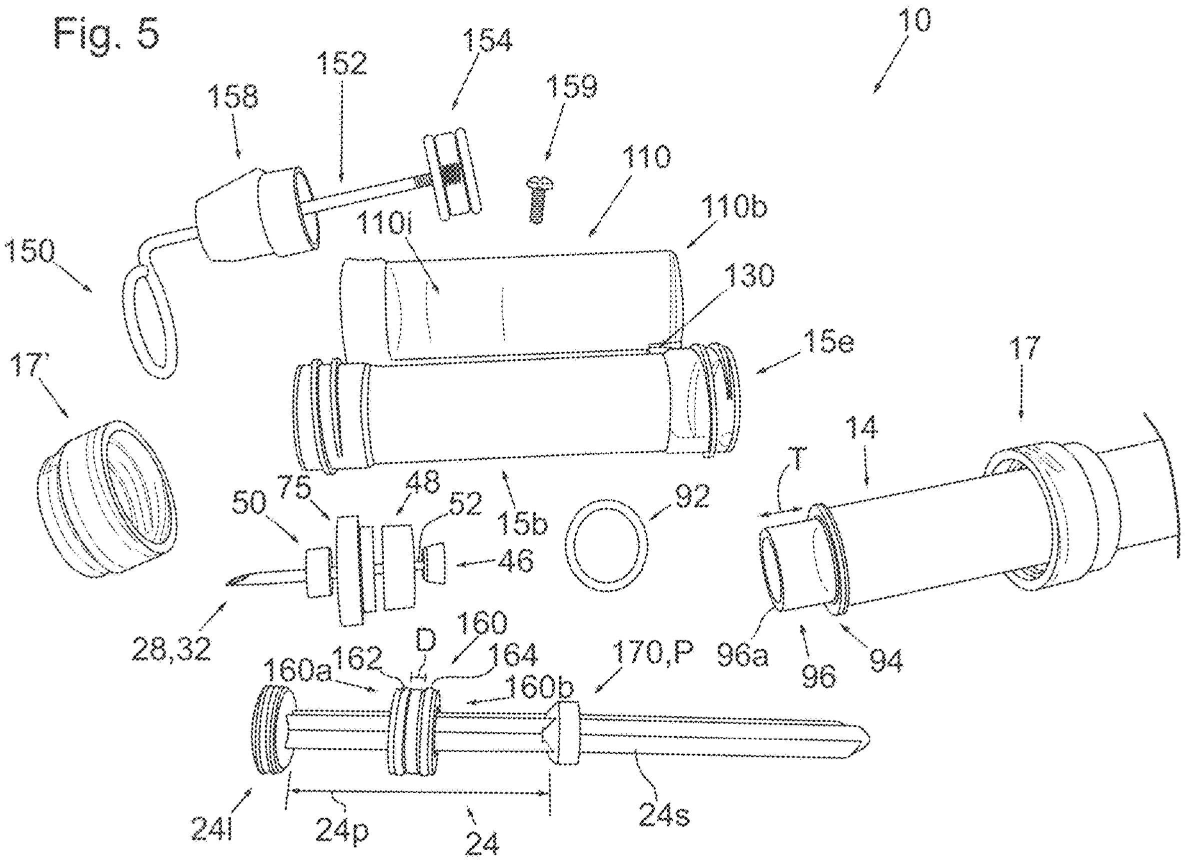
FIG. 5 is an exploded perspective view of the self-removing animal dart of FIG. 3.

As noted above, the syringe 15 may be threadably connected to the shaft 14 via threadable connector 17. More preferably, and as shown in FIGS. 2 and 5, shaft 14 has a tubular connector 96 having a leading edge 96*a* and shaped to fit within the first end 15*e* of the syringe 15. An annular seal 92 may slide over the tubular connector 96 and rest against a tab 94 of the tubular connector 96 to prevent air leakage from the first pressure chamber 22 when the dart 10 is fully assembled. Tab 94 may be set back a predetermined tab distance T from leading edge 96*a*. Connector 17 is threadably connected to the first (trailing) end 15*e* of the syringe 15 to secure the syringe 15 to the first pressure chamber 22. The connector 17 and trailing end 15*e* of the syringe 15 can be rotated with respect to the shaft 14 allowing the user to rotatably adjust the position of the contact member 50 relative to the shaft 14. When the threaded connection between connector 17 and trailing end 15*e* of the syringe 15 is tightened, tab 94 may be moved towards the syringe 15, squeezing annular seal 92 and preventing rotation of the syringe 15 with respect to the shaft 14 while the threaded connection is tightened.

Figure 3:
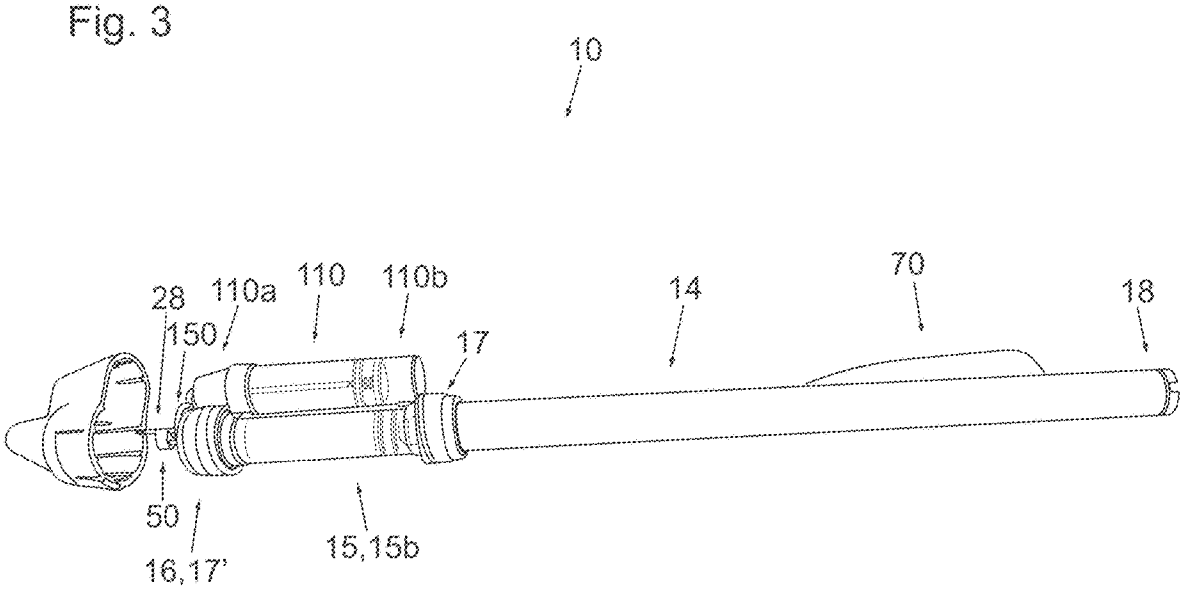
FIG. 3 is a perspective view of another embodiment of a self-removing animal dart, wherein some of the components are constructed of a transparent material.

Flights 70 may be positioned at the second end 18 of the shaft 14 to stabilize the flight of the dart 10 (see FIG. 3). In order for a user to orient the syringe 15 more easily to position the first contact member 50 below the when the dart 10 is used, the flights may be asymmetric or differentially coloured and the user may be instructed to align the first contact member 50 and needle 28 in a known orientation with respect to the flights 70. The flights 70 may act as a guide to aligning the dart 10.

Figure 4:
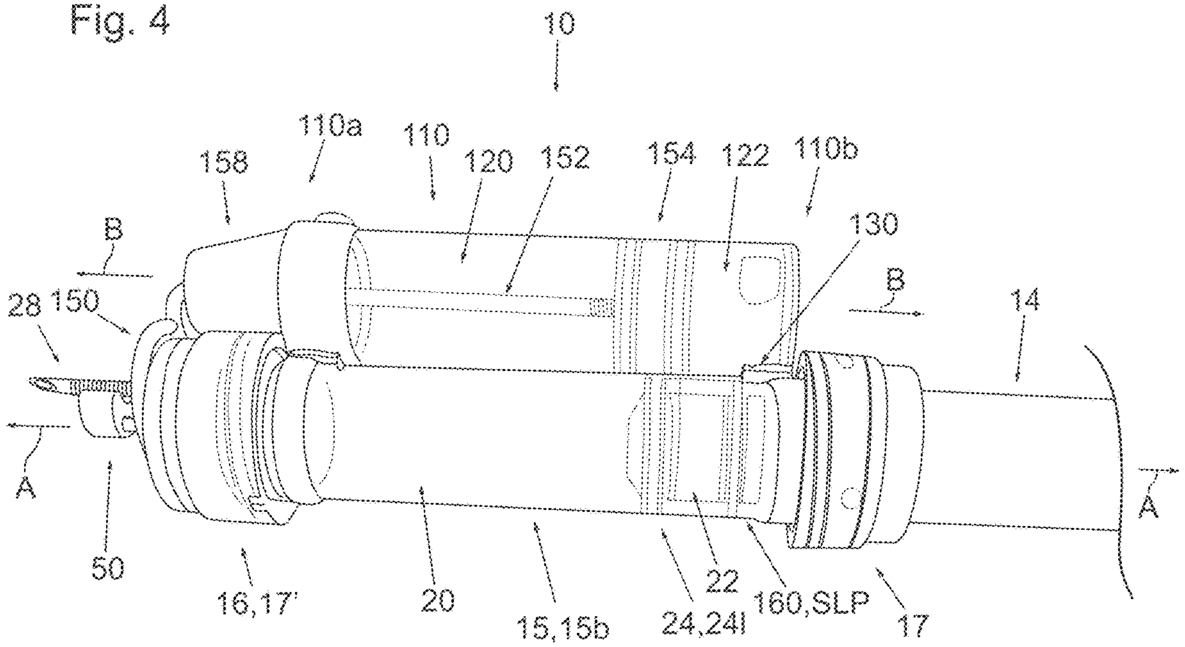
FIG. 4 is another perspective view of the self-removing animal dart of FIG. 3.
Figure 6A:
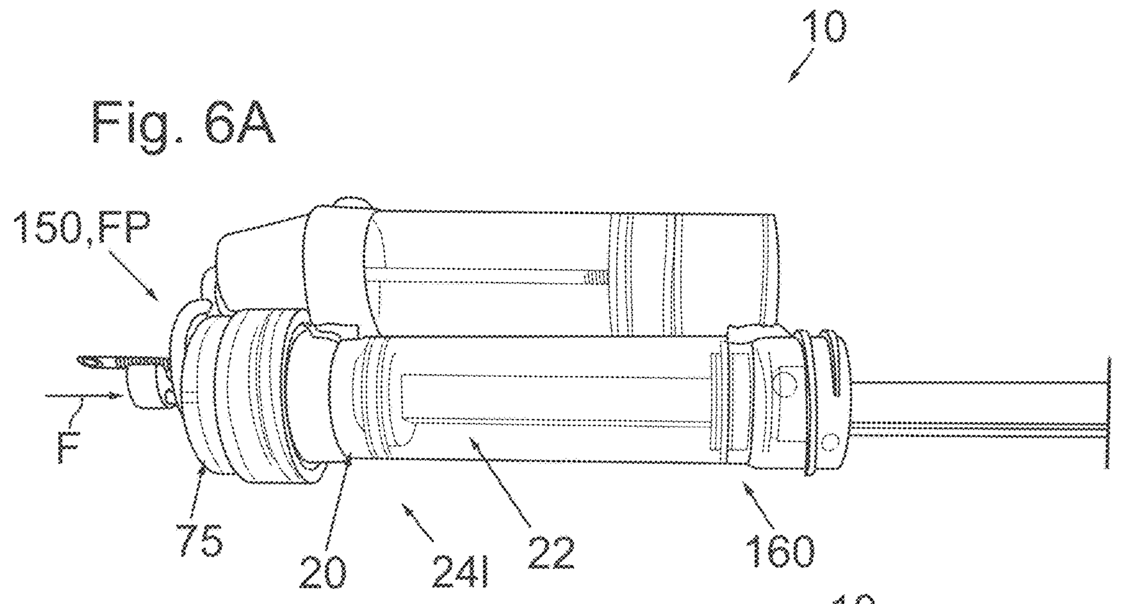
FIGS. 6A-6L are perspective views of the self-removing animal dart of FIG. 3, illustrating the various stages of loading liquid medication into the syringe, ejecting the liquid medication out through the needle, and actuating the first and second contact members to disengage the dart from the animal's hide.
Figure 6B:
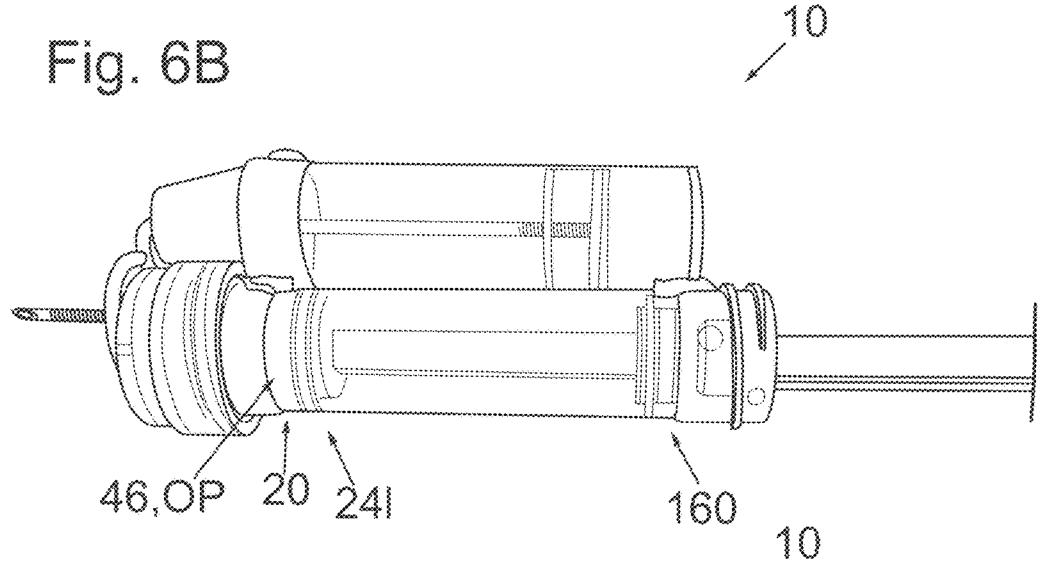
Figure 6C:
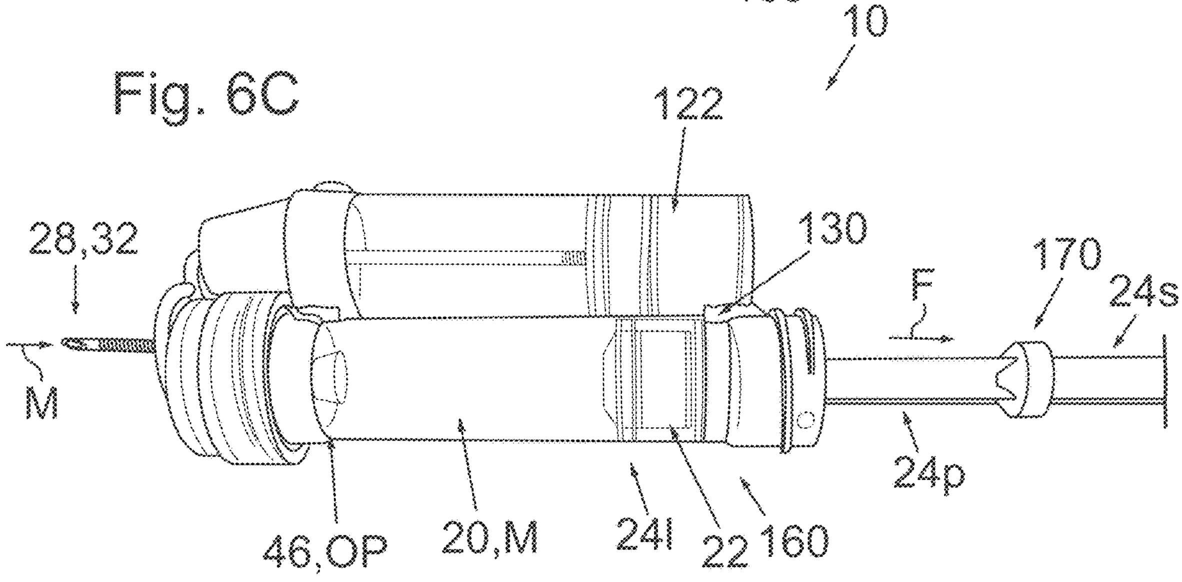
Figure 6D:
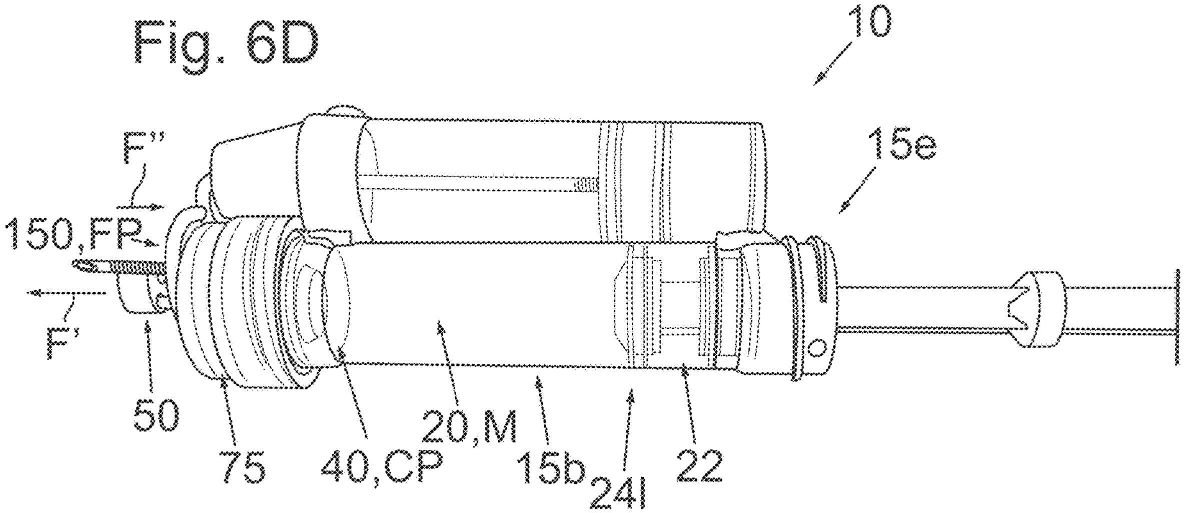
Figure 6E:
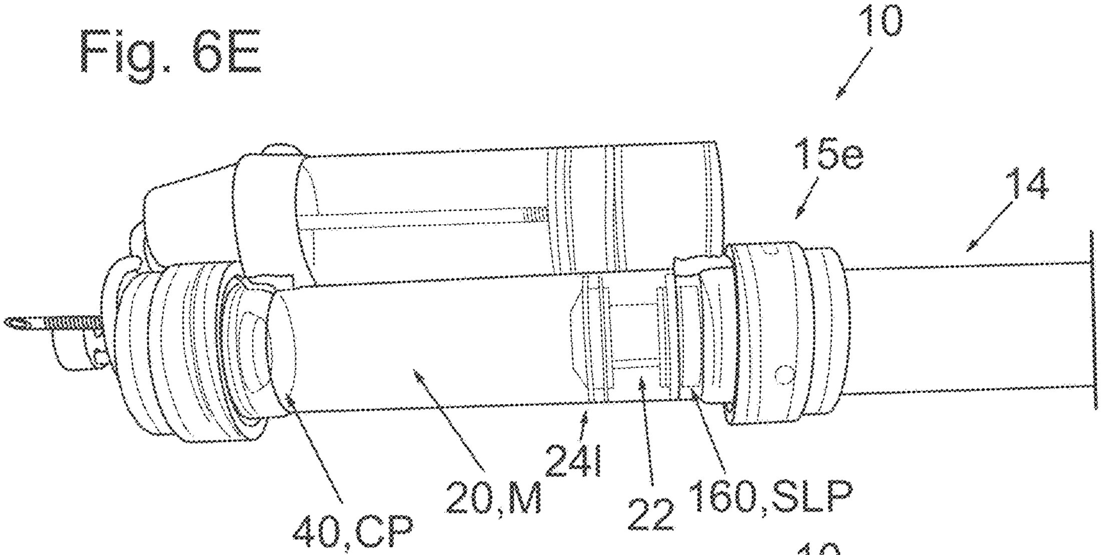
Figure 6F:
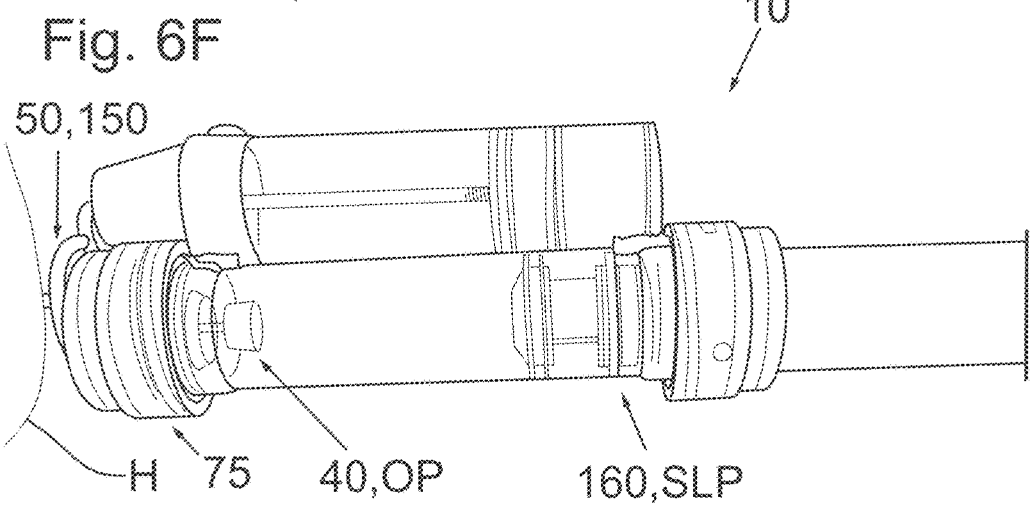
Figure 6G:
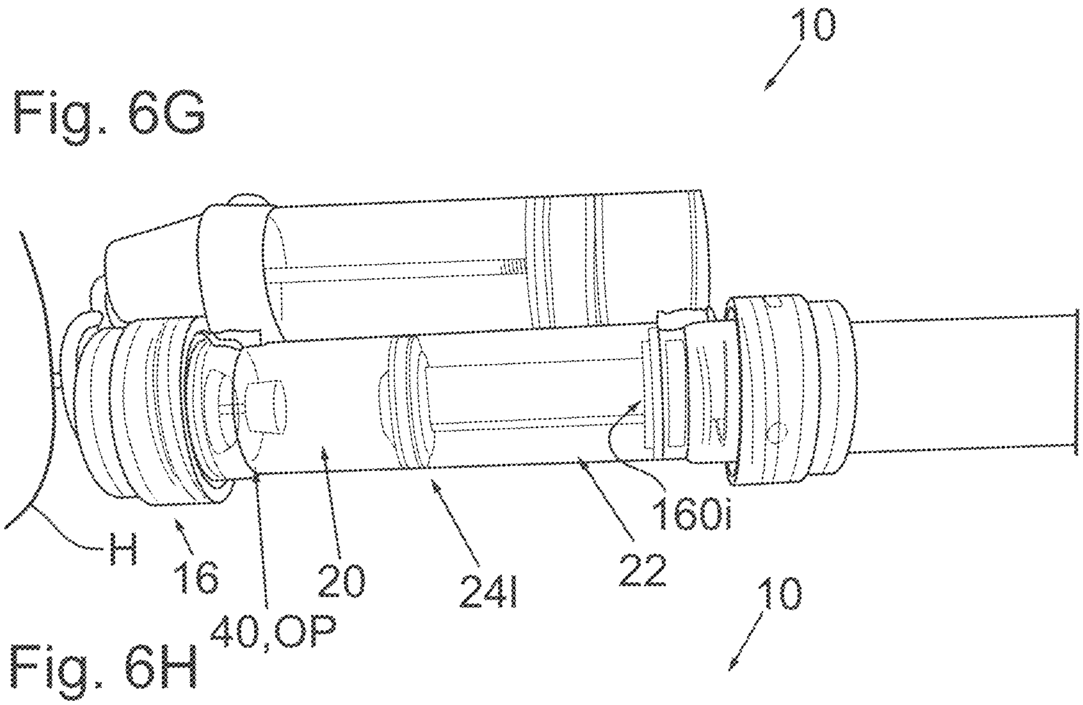
Figure 6H:
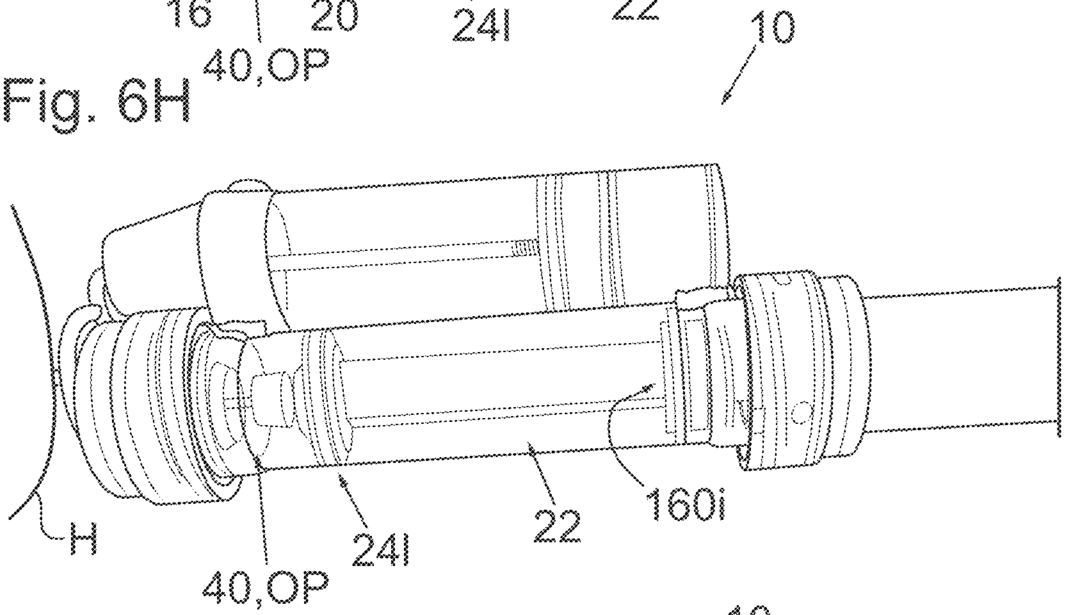
Figure 6I:
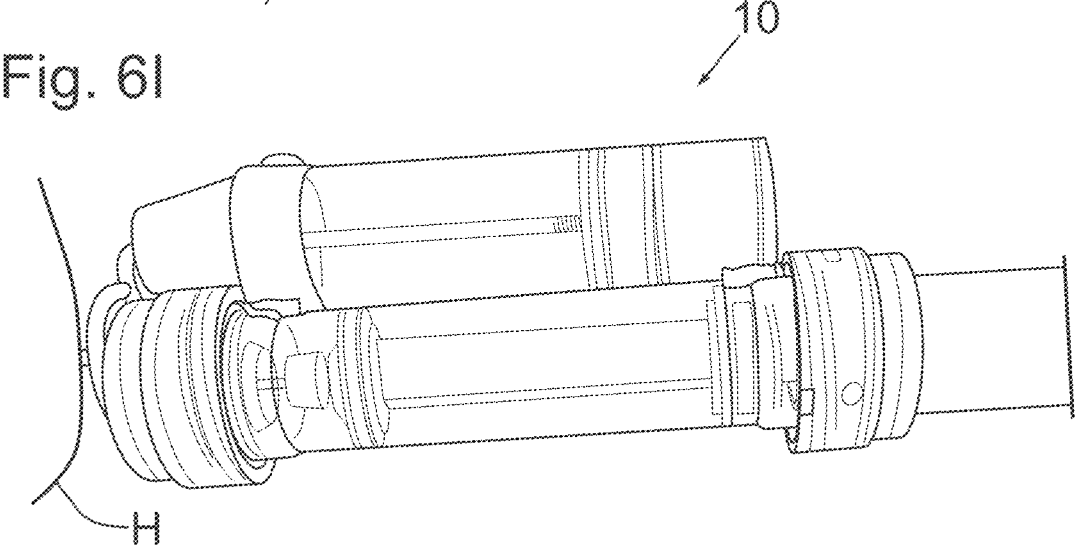
Figure 6J:
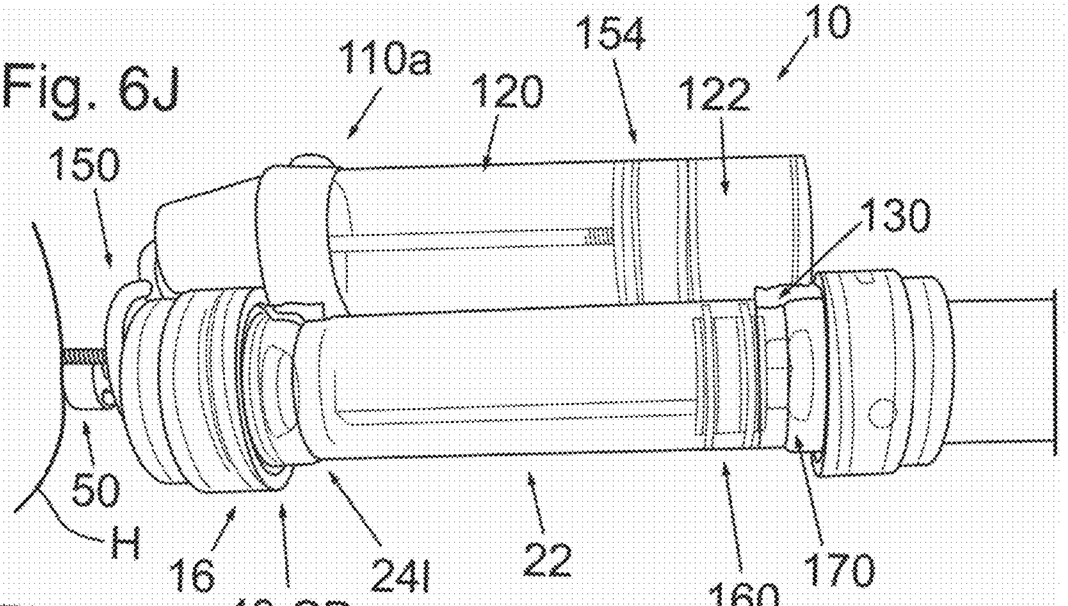
Figure 6K:
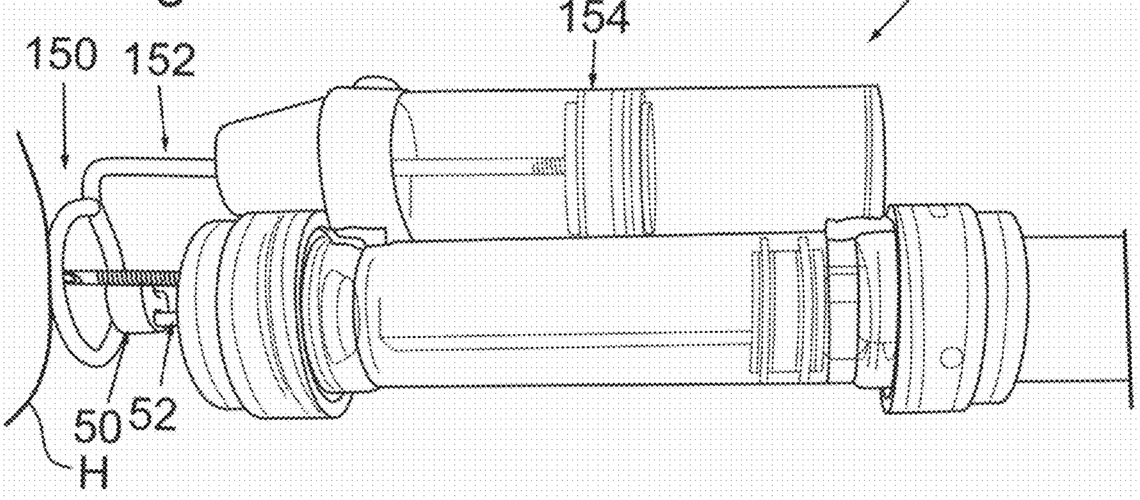

First contact member 50 may be any shape, for example substantially semi-circular as shown in FIGS. 4 and 6K (and as taught in U.S. Patent Application Publication No. 2019/0249965) or substantially shaped as a loop around the needle 28. First contact member 50 may have an indentation 54 shaped to accommodate the needle 28. However, preferably the first contact member 50 does not extend around the needle 28, the indentation 54 being adjacent to only one side of the needle. The first contact member 50 is preferably positioned less forward than the tip 32 of the needle 28 so that if the dart 10 hits the animal reasonably close to perpendicular to the hide H of the animal, the needle 28 will hit the animal's hide H before hitting the first contact member 50.

When valve 40 is in the closed position CP (e.g. FIGS. 6*d*, 6*e* and 7) with valve member 46 positioned in passage 44, first contact member 50 is positioned away from first end 16 of the shaft 14, and is closer towards the needle's tip 32. When valve 40 is in the open position OP (e.g. FIGS. 6*b* and 6*f*), with valve member 46 spaced from passage 44, first contact member 50 is positioned closer to first end 16 of the shaft 14.

Valve 40 may be secured to the first end 16 of shaft 14 via a second threaded connection 15*e*' and second treaded connector or end cap 17'. Valve 40 has an annular spacer or valve seat member 48 that has passage 44 extending therethrough.

The needle 28 preferably may be in fluid communication with the syringe 15, via passage 44, regardless of the needle's circumferential position relative to the annular spacer 48. The annular spacer or seat member 48 may have a fluid passage connecting passage 44 to annular cavity (as taught in U.S. Patent Application Publication No. 2019/0249965). A needle mounting disk 75 may be provided to secure needle 28 to the syringe 15, as well as to support or mount the first contact member 50, the first rigid coupling 52 and the valve member 46.

The self-removing animal dart 10 further comprises a support member 110 having a hollow internal cavity 110*i*. The support member 110 supports a second contact member 150. Support member 110 is preferably a cylindrical member or barrel, having a first (leading) end 110*a*, a second (trailing) end 110*b*, and a center axis B. Center axis B may also be referred to as support member center axis B or second axis B. The support member 110 is preferably positioned on, or mounted to, one side of the syringe barrel 15*b* so that support member's first end 110*a* is closest to the first end 16 of the shaft, so that its second end 110*b* is closest to the second end 18 of the shaft 14, and so that its center axis B is positioned substantially parallel to one side of the center axis A of the dart (see FIG. 4). In a preferred embodiment, support member 110 is mounted above the syringe 15 (when the dart 10 is in an operating position). Preferably, the support member 110 and syringe barrel 15*b* are a single piece, e.g. constructed from a single molded transparent plastic (see FIG. 5). More preferably, support member 110 has a similar outside diameter as the diameter of the syringe barrel 15*b*.

Second contact member 150 may be supported by support member 110 via a rigid coupling 152. Second contact member 150 is movable axially in relation to needle 28 and functions to disengage, or assist with the disengagement of, the dart 10 from an animal (not shown) once the liquid medication M has been injected into the animal. Preferably second contact member 150 is positioned at or near the center axis A of the shaft of the dart 10, and the needle 28 is positioned to one side relative to the center axis A of the dart 10 (see FIG. 4). Second contact member 150 may be any shape, for example a substantially circular loop extending around both the needle 28 and the first contact member 50 (see FIG. 6K) or shaped as a semi-circular member. Second contact member 150 may be a loop having a substantially similar outside diameter as the outside diameter of the shaft 14.

Figure 6L:
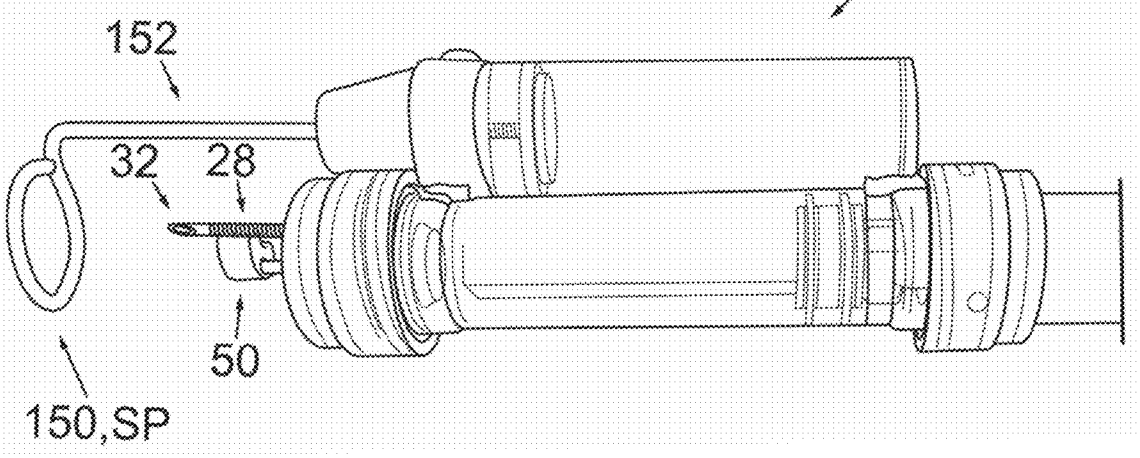

The second contact member 150 may be movable between a first position FP, wherein it is closest to the mounting disk 75 and first end 16 (see FIGS. 3 and 6*a*) and a second position SP, wherein it is furthest from the mounting disk 75 and wherein it extends axially (along axis A) beyond the needle's tip 32 so that it can function to disengage, or assist with the disengagement of, the dart 10 from an animal (see FIGS. 1 and 6*l*). In this manner, the second contact member 150 functions as a second disengaging member 150. The rigid coupling 152, which may be a rod, couples the movement of second contact member 150 and a second piston 154. A rod mounting cap 158 is preferably provided to slidable, sealable secure rigid coupling 152 through the first end 110*a* of the support member 110. A set screw 159 may be provided to secure the rod mounting cap 158 to said first end 110*a*.

Second piston 154 is slidable, sealably disposed within the internal cavity 110*i* of the support member 110. Piston 154 is slidable (movable) within the internal cavity 110*i* along axis B between the first and second ends 110*a*, 110*b*. Piston 154 fits tightly within the internal cavity 110*i* and functionally separates the internal cavity 110*i* into a coupling chamber 120 and a second pressure chamber 122. The second pressure chamber 122 is preferably constructed in a conventional manner and of suitable material (e.g. moulded plastic or steel) to provide adequate strength, durability, sealability and rigidity to support the various loads and pressures that may be encountered and/or required to actuate the various components of the dart 10.

A coupling chamber 120 may be provided fluid communication access to the external atmosphere, e.g. via a small passage (not shown), so as to allow the piston 154 to easily slide within the internal cavity 110*i*; e.g. in response to an increase in air pressure within second pressure chamber 122. The second pressure chamber 122 communicates with the first pressure chamber 22 via linking passage 130. As such, pressurized air in the first pressure chamber 22 may provide the motive force (directly or indirectly, e.g. via passage 130 into second pressure chamber 122 and acting on second piston 154) to power and allow the second disengaging member 150 to disengage the dart 10 from an animal.

Except for said linking passage 130, the interior 15*i* of the syringe barrel 15*b* and the interior 110*i* of the support member 110 are fluidly isolated from each other.

The self-removing animal dart 10 further comprises a sliding valve 160 slidably disposed about the plunger shaft 24*s* and captured thereon by a capture member 170. Capture member 170 may be slidable, releasably secured to the plunger shaft 24*s* at a desired position P. A set screw 172 may be provided to lock the capture member 170 at the desired position P along the plunger shaft 24*s*. It is contemplated that sliding valve 160 is slidably disposed about the plunger shaft 24*s* in such a manner that there is minimal friction therebetween and so that these two components 24*s*, 160 can slide or move relative to each other with minimal force required to do so. Once captured on the plunger shaft 24*s*, sliding valve 160 can slide along a portion 24*p* of the plunger shaft 24*s* between the plunger seal 241 and the locking member 170. Likewise, the portion 24*p* of the plunger shaft 24*s* can easily slide through sliding valve 160 when sliding valve is maintained at a sealing position SLP within the dart 10 (e.g. see FIG. 6*f* vs 6*g*).

Sliding valve 160 has a leading end 160*a* and a trailing end 160*b*. Sliding valve 160 is preferably an annular cylindrical member wherein the interior passage or interior diameter 160*i* is of sufficient size to easily slide over the plunger shaft 24*s* and to also provide fluid communication of any pressurized air P therethrough, i.e. to allow pressurized air P to move between leading and trailing ends 160*a*, 160*b*

Figure 7:
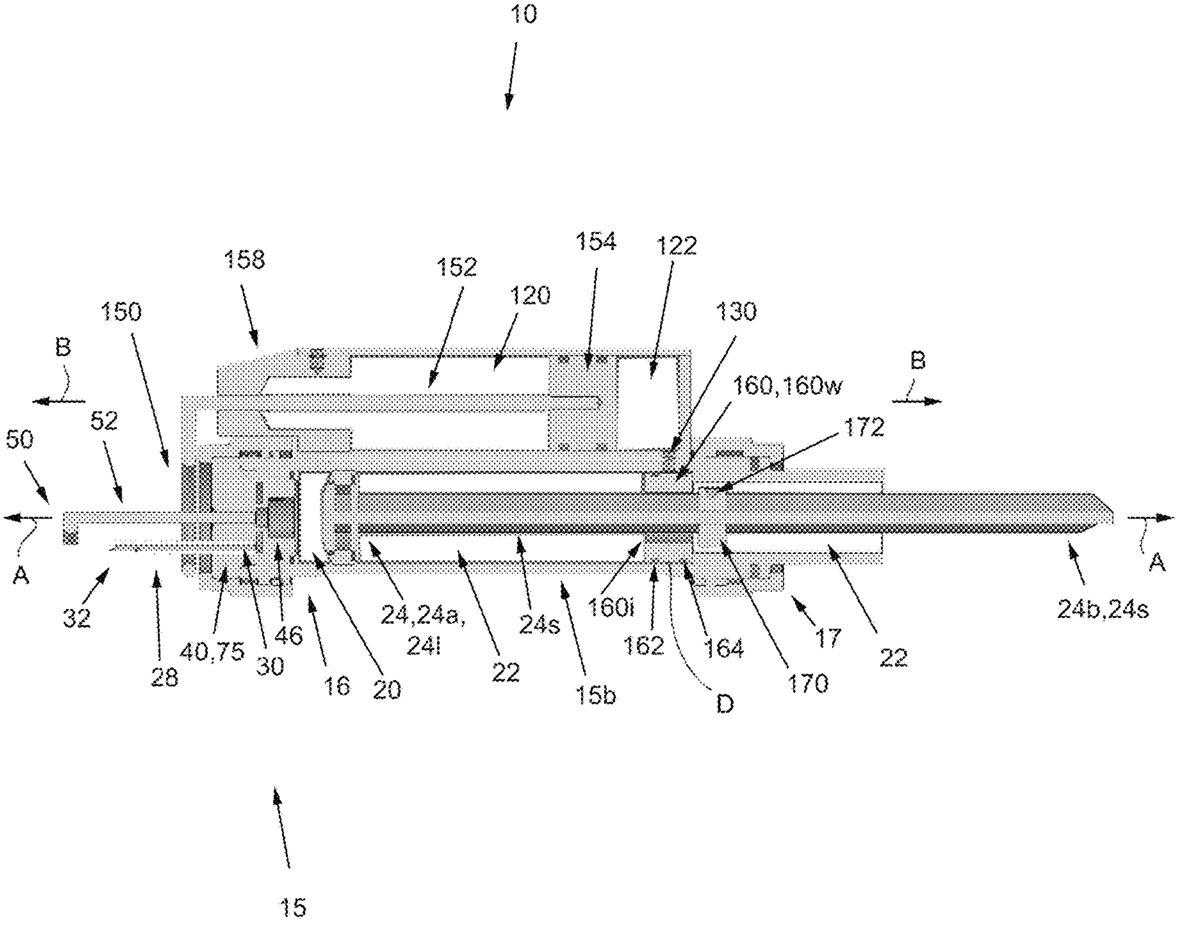
FIG. 7 is a sectioned view of the self-removing animal dart of FIG. 3.

(see FIG. 7). Alternatively, in another embodiment (not shown) sliding valve 160 may be provided with one or more passages therethrough to provide fluid communication between the leading and trailing ends 160*a*, 160*b*. Sliding valve 160 further comprises an annular circumferential wall or perimeter 160*w* that is suitable to prevent fluid communication of any pressurized air or pressurized fluids from the interior 160*i* to the exterior of the annular wall 160*w*; i.e. any fluid communication of pressurized air P through sliding valve 160 is then only through the interior passage 160*i* between the leading and trailing ends 160*a*, 160*b*.

Sliding valve 160 may be provided with a leading seal 162 (at leading end 160*a*) and a trailing seal 164 (at trailing end 160*b*). The leading and trailing seals 162, 164 sealably dispose the sliding valve 160 within the first pressure chamber 22 within the syringe barrel 15*b*. The leading and trailing seals 162, 164 may be provided on the sliding valve at a predetermined distance D from each other (e.g. see FIG. 5). Preferably, both the leading seal 162 and the trailing seal 164 fit tightly, but slidably, within the first pressure chamber 22 of the syringe barrel 15*b* when the sliding valve 160 is placed therewithin. More preferably, the friction of the tight fit of sliding valve 160 to the interior of the syringe barrel 15*b* (provided by seals 162, 164) is greater than friction between the plunger shaft 24*s* as it moves through the sliding valve 160. Advantageously, when the sliding valve 160 is placed at the sealing position SLP, the plunger shaft 24*s* can easily slide through valve 160 without dislodging the valve 160 from the sealing position SLP.

Preferably, distance D along the annular wall 160*w* is of sufficient size to fully seal passage 130 and prevent fluid communication between the first and second pressure chambers 22, 122 (due to the presence of seals 162, 164) when the sliding valve 160 is positioned at the sealing position SLP (e.g. see FIG. 4). More preferably, the tab distance T of the shaft's tab 94 is preset or predetermined so that, when the sliding valve 160 is inserted into the syringe barrel 15*b* at the first threaded end 15*e*, the leading edge 96*a* of the tubular connector 96 will position the sliding valve 160 to the sealing position SLP when the threaded connection between connector 17 and first threaded end 15*e* of the syringe 15 is tightened.

To fill syringe chamber 20 with medication M, valve 40 is placed into an open position OP by exerting a force F upon the first contact member 50 until first contact member 50 moves toward mounting disk 75 (and first end 30 of needle 28) thereby pushing rigid coupling 52 and valve member 46 out of passage 44 (see FIGS. 6*a*-6*b*). Medication M may then be inserted (or drawn up) through needle 28 into syringe chamber 20, such as by exerting a force F on the plunger shaft 24*s* to draw the plunger's seal 241 away from the valve 40, thereby creating negative or reduced pressure within the syringe chamber 20 (with respect to the external atmosphere; see FIG. 6*c*).

Once there is a desired amount of medication M in the syringe chamber 20, a force F' may then exerted upon first contact member 50, pulling it away from the mounting disk 75 until the valve 40 is placed into a closed position CP, as illustrated in FIG. 6*d*. This draws valve member 46 into passage 44, placing valve 40 into the closed position CP. If necessary, and before the sliding valve 160 is placed in the sealing position SLP and before the dart 14 is fully assembled, a force F" may be applied to the second contact member 150 to move it to the first position FP (if it wasn't already in the first position FP). Since sliding valve 160 is not yet into the sealing position SLP, piston 154 will more easily slide within the internal cavity 110*i*, as any excess air pressure that may be in the second pressure chamber 122 (due to pistion 154 moving towards second end 110*b*) can exit through the linking passage 130 into the first pressure chamber 22 and out the trailing end 15*e* of the syringe.

Shaft 14 may then be connected to the trailing end 15*e* of the syringe 15, thereby fully assembling the dart 10, sealing first pressure chamber 22, moving the leading edge 96*a* the predetermined tab distance T into the trailing end 15*e* of the syringe barrel 15*b*, and positioning the sliding valve 160 to the sealing position SLP (see FIG. 6*e*). Once the sliding valve 160 is in the sealing position SLP fluid communication between the first and second pressure chambers 22, 122 is prevented by said valve 160. A needle valve 60 may then be inserted into self-sealing passage 36 of rubber plug 34. Air may then pumped through the needle valve 60 and the self-sealing passage 36, for example using a bicycle pump 62, to pressurize first pressure chamber 22; and because of sliding valve 160 being in the sealing position SLP, any such pressurized air in the first pressure chamber 22 will be prevented from entering the second pressure chamber 122. Due to the presence of movable plunger 24, and the plunger seal 241, disposed between first pressure chamber 22 and syringe chamber 20; the pressurization of first pressure chamber 22 places medication in syringe chamber 20 under equal pressure with pressure chamber 22.

When needle 28 enters the hide H of an animal, first contact member 50 is pushed toward mounting disk 75 by the hide H; see FIG. 6*f*. Needle 28 may be suited for intra-muscular injections or for subcutaneous injections as may be desired. As first contact member 50 moves towards mounting disk 75, valve member 46 is also moved until valve 40 is in the open position OP; see FIG. 6*f*. Accordingly, movement of the first contact member 50 actuates the valve into the open position OP. Once valve 40 is in the open position OP a differential in pressure is created as between syringe chamber 20 and first pressure chamber 22. First pressure chamber 22 remains under pressure, whereas the pressure in first syringe chamber 20 is released via needle 28.

The greater air pressure within pressure chamber 22 causes plunger 24, and plunger seal 241, to move toward the first end 16 of the dart 10, shortening the length of syringe chamber 20 and sending liquid medication M in syringe chamber 20 past open valve member 46 along passage 44 and through needle 28 until liquid medication has vacated syringe chamber 20 (and entered the animal through it's hide H); see FIGS. 6*g*-6*i*. The greater air pressure in the first pressure chamber 22 will initially pass-through interior passage 160*i* to exclusively act on plunger seal 241. Sliding valve 160 will remain in the sealing position SLP, preventing fluid communication between the first and second pressure chambers 22, 122, until acted upon by capture member 170.

The plunger head or seal 241 eventually contacts the valve member 46 and pushes the valve member 46 forward into passage 44, moving the valve to the closed position CP, and moving first contact member 50 toward the second end 32 of the needle 28, as shown in FIG. 6*j*. Accordingly, movement of the plunger seal 241 against valve member 46 actuates the valve 40 into the closed position and moves or operates first contact member 50 to, at least partially, disengage the dart 10 from the hide H of an animal (see FIGS. 6*i*-6*j*). In this manner, the first contact member 50 functions as a first disengaging member 50. On or about that same time, capture member 170, which is locked at the desired position P on the plunger shaft 24*s*, contacts the sliding valve 160, moving said sliding valve 160 towards the leading end 15*e*' of the syringe barrel 15*b* and out of the sealing position SLP and allowing for fluid communication between the first and second pressure chambers 22, 122 via linking passage 130; see FIG. 6*j*.

The timing of when exactly the capture member 170 contacts the sliding member 160 (relative to when the plunger seal 241 contacts the valve member 46) may be adjusted by releasing said capture member 170 from the plunger shaft 24*s* (e.g. by releasing set screw 172), and then re-securing said member 170 at a new desired position P along the plunger shaft 24*s* (e.g. by tightening the set screw 172).

Once the sliding valve 160 is moved out of the sealing position SLP, the greater air pressure present in the first pressure chamber 22 can now enter the second pressure chamber 122 (via linking passage 130). This greater air pressure in second pressure chamber 122 will then act on piston 154 moving it to the first (leading) end 110*a* of the support member 110. As piston 154 moves to the first (leading) end 110*a*, it moves the second contact member 150 to the second position SP (via the second rigid coupling 152); see FIGS. 6*j*-6*l*.

Due to the presence of the first rigid coupling 52, the movement of valve member 46 serves to move first contact member 50 toward second end 32 of needle 28. Due to the presence of rigid coupling 152, the movement of piston 154 serves to move second contact member 150 toward second end 32 of needle 28 (see FIG. 6*k*), and eventually beyond the tip 32 of the needle to the second position SP (see FIG. 6I).

Advantageously, the first and/or second contact members 50, 150 (i.e. first and second disengaging members 50, 150) cooperate together to disengage or pull needle 28 out of the hide H of an animal. More advantageously, the pressure or force exerted by both the first and second contact members 50, 150 against the animal's hide H is greater than prior art devices, significantly increasing the likelihood that the dart 10 disengages from the animal, thereby allowing the dart 10 to promptly drop away from the animal once the medication M has been delivered. Even more advantageously, by moving the second contact member 150 axially beyond the needle's tip 32, along axis A, the dart 10 of the present invention is more efficient at dislodging from an animal's hide.

Those of ordinary skill in the art will appreciate that various modifications to the invention as described herein will be possible without falling outside the scope of the invention. In the claims, the word "comprising" is used in its inclusive sense and does not exclude other elements being present. The indefinite article "a" before a claim feature does not exclude more than one of the features being present.

The invention claimed is:

1. A self-removing animal injection apparatus for injecting an animal with a liquid medication (M), the apparatus (10) comprising:
- a shaft (14) having a first end (16);
- a syringe (15);
- a needle (28) at said first end (16) of the shaft (14) and defining a longitudinal direction, the needle (28) being in fluid communication with the syringe (15);
- a first disengaging member (50) movable substantially along the longitudinal direction and operable to assist with disengagement of the animal injection apparatus (10) from the animal once at least some of the liquid medication (M) has been injected into the animal;
- a second disengaging member (150) movable substantially along the longitudinal direction and operable to assist with disengagement of the animal injection apparatus (10) from the animal once at least some of the liquid medication (M) has been injected into the animal; and
- wherein at least one source of pressure provides a motive force to move each of the first and second disengaging members (50, 150);

the self-removing animal injection apparatus further comprising:
- a needle mounting disk (75) to secure the needle (28) to the syringe (15) and to support the first disengaging member (50); and
- a support member (110) to support the second contact member (150);
- a first pressure chamber (22);
- wherein the support member (110) further comprises a hollow internal cavity (110*i*) having a second pressure chamber (122);
- wherein the first pressure chamber (22) is operable to contain a first source of pressure;
- wherein the second pressure chamber (122) is operable to contain a second source of pressure;
- wherein said first and second sources of pressure provide the motive force to move the first disengaging member (50) and the second disengaging member (150) along the longitudinal direction;
- wherein the first pressure chamber (22) fluidly communicates with the second pressure chamber (122) via a linking passage (130);
- wherein the syringe (15) further comprises a syringe barrel (15*b*) having an interior (15*i*);

the self-removing animal injection apparatus further comprising:
- a plunger (24) having a plunger shaft (24*s*), wherein the plunger shaft (24*s*) reciprocates within the syringe barrel (15*b*) and the first pressure chamber (22);
- a sliding valve (160) slidably disposed about the plunger shaft (24*s*) and captured thereon by a capture member (170);
- wherein, when the sliding valve (160) is positioned at a sealing position (SLP) fluid communication between the first and second pressure chambers (22, 122) is prevented.

2. The self-removing animal injection apparatus of claim 1 wherein when the capture member (170) contacts the sliding valve (160), said sliding valve (160) is moved out of the sealing position (SLP) and allows for fluid communication between the first and second pressure chambers (22, 122) via the linking passage (130).

* * * * *